(12) United States Patent
Lee et al.

(10) Patent No.: US 12,133,927 B2
(45) Date of Patent: Nov. 5, 2024

(54) HYBRID POWER SUPPLY SYSTEMS, METHODS, AND DEVICES FOR EXCIMER LAMPS

(71) Applicant: GOODRICH CORPORATION, Charlotte, NC (US)

(72) Inventors: Yongduk Lee, Vernon, CT (US); Matthew Robert Pearson, Hartford, CT (US)

(73) Assignee: GOODRICH CORPORATION, Charlotte, NC (US)

( * ) Notice: Subject to any disclaimer, the term of this patent is extended or adjusted under 35 U.S.C. 154(b) by 481 days.

(21) Appl. No.: 17/506,573

(22) Filed: Oct. 20, 2021

(65) Prior Publication Data

US 2023/0118585 A1   Apr. 20, 2023

(51) Int. Cl.
*A61L 2/10* (2006.01)
*A61L 9/20* (2006.01)
*H01J 61/56* (2006.01)
*H01J 65/04* (2006.01)
*H05B 41/28* (2006.01)

(52) U.S. Cl.
CPC .............. *A61L 2/10* (2013.01); *A61L 9/20* (2013.01); *H01J 61/56* (2013.01); *H01J 65/048* (2013.01); *H05B 41/2806* (2013.01); *A61L 2202/11* (2013.01)

(58) Field of Classification Search
CPC .......... A61L 2/10; A61L 9/20; A61L 2202/11; A61L 2202/14; A61L 2202/25; H01J 61/56; H01J 65/048; H05B 41/2806; H05B 41/282; B64D 2011/0038; B64D 2011/0053
See application file for complete search history.

(56) References Cited

U.S. PATENT DOCUMENTS

| 4,199,703 A | 4/1980 | Samson |
| 4,589,123 A | 5/1986 | Pearlman et al. |

(Continued)

FOREIGN PATENT DOCUMENTS

| CN | 108093551 | 3/2020 |
| JP | 2004350338 | 12/2004 |
| JP | 06233025 | 11/2017 |

OTHER PUBLICATIONS

Mame Andallah Diop, "Alimentation sans transformateur pour dispositif de decharge a barriere dielectrique (DBD)", Universite de Toulouse, dated Oct. 23, 2018, pp. 94-103, XP093024445, Retrieved from the Internet: url: https://theses.hal.science/tel-01902468, [retrieved on Feb. 16, 2023].

(Continued)

*Primary Examiner* — Jason L McCormack (74) *Attorney, Agent, or Firm* — SNELL & WILMER L.L.P.

(57) ABSTRACT

A sanitization apparatus includes an excimer lamp and a power converter. The power converter comprises a wide band gap device and a planar inductor. The wide band gap device is selectively switchable between a first mode wherein the inductor is electrically charged and a second mode wherein the inductor is electrically discharged. The wide band gap may be repeatedly switched between the first and second modes to generate a nano second pulse output voltage waveform.

12 Claims, 8 Drawing Sheets

(56) References Cited

U.S. PATENT DOCUMENTS

| | | | |
|---|---|---|---|
| 6,194,828 B1 | 2/2001 | Kohne et al. | |
| 6,633,093 B1 | 10/2003 | Rim et al. | |
| 10,080,275 B2 | 9/2018 | Bourke, Jr. et al. | |
| 10,974,493 B2 | 4/2021 | Fathi | |
| 2002/0070177 A1* | 6/2002 | Kozlowski | H05B 41/3925 210/748.11 |
| 2003/0011319 A1* | 1/2003 | Hein | H05B 41/2827 315/224 |
| 2019/0139753 A1* | 5/2019 | Skinner | H05B 41/2806 |
| 2020/0368468 A1* | 11/2020 | Liu | A61L 9/20 |
| 2021/0298391 A1* | 9/2021 | Keene | A41D 13/1192 |

OTHER PUBLICATIONS

Diop, et al, "10 kV SiC MOSFET Evaluation for Dielectric Barrier Discharge Transformerless Power Supply", Plasma, vol. 3, No. 3, dated Aug. 18, 2020, pp. 103-116, XP093024419, DOI: 10.3390/plasma3030009.

Lefranc, et al, "Optimisation and characterization of plantar transformer with high voltage ration and high output voltage for plasma reactors", IET Power Electronis, vol. 8, No. 6, dated Dec. 31, 2015, pp. 929-937, XP006052397, ISSN: 1755-4535, DOI: 10.1049/IET-PEL.2014.0139.

Rueda, et al, "Optimum transformer turns ration for the power supply of dielectric barrier discharge lamps", IET Power Electronics, vol. 11, No. 1, dated Jan. 12, 2018, pp. 62-67, XP006065167, ISSN: 1755-4535, DOI: 10.1049/IET-PEL.2016.0497.

European Patent Office, European Search Report dated Feb. 27, 2023 in Application No. 22199637.4.

* cited by examiner

HYBRID POWER SUPPLY SYSTEMS, METHODS, AND DEVICES FOR EXCIMER LAMPS

FIELD

The present disclosure relates generally to sanitization systems and methods and, more particularly, to power supply systems and methods for ultraviolet (UV) light sanitization systems.

BACKGROUND

The recent novel-coronavirus (SARS-COV-2) outbreak has negatively impacted the safety and health of many people. Pathogens can be transmitted via direct airborne transmission between users or via indirect contact transmission from different users occupying the same space at different times. For example, lingering pathogens may remain on contact surfaces of an aircraft cabin to be spread to passengers and/or crew members on a subsequent flight. The safety of passengers and crew members may be improved by performing disinfecting treatments to surfaces, such as seats, ceiling/wall panels, handles, and lavatory surfaces, etc., to mitigate the presence of pathogens on such surfaces. However, conventional disinfection procedures between flights may take time and may thus adversely affect the operating efficiency of the aircraft (increased interval time between flights), and the effectiveness and quality of such conventional treatments are often difficult to verify/track.

SUMMARY

A sanitization apparatus is disclosed, comprising an excimer lamp, and a power converter comprising a wide band gap device and an inductor, wherein the wide band gap device is selectively switchable between a first mode wherein the inductor is configured to be electrically charged and a second mode wherein the inductor is configured to be electrically discharged to the excimer lamp.

In various embodiments, the excimer lamp is configured to emit Far-UVC light.

In various embodiments, the wide band gap device comprises a transistor.

In various embodiments, the inductor is a planar inductor.

In various embodiments, the power converter comprises a printed circuit board, wherein the inductor is embedded in the printed circuit board.

In various embodiments, the printed circuit board comprises a first layer comprising the inductor and a second layer comprising the wide band gap device, wherein the wide band gap device is embedded in the printed circuit board.

In various embodiments, the wide band gap device is in an ON state in the first mode and the wide band gap device is in an OFF state in the second mode.

In various embodiments, the sanitization apparatus further comprises a DC power supply configured to charge the inductor when the wide band gap device is in the second mode.

In various embodiments, the inductor is connected across the excimer lamp.

A power converter for an excimer lamp is disclosed. The power converter comprises a wide band gap device switchable between a first mode and a second mode, and a planar inductor configured to receive an electric power in response to the wide band gap device switching to the first mode and configured to discharge the electric power into the excimer lamp in response to the wide band gap device switching to the second mode.

In various embodiments, the wide band gap device comprises a transistor selectively switchable between an ON state in the first mode and an OFF state in the second mode.

In various embodiments, the power converter further comprises a printed circuit board comprising the wide band gap device and the planar inductor.

In various embodiments, the first planar inductor is embedded in the printed circuit board.

In various embodiments, the wide band gap device is embedded in the printed circuit board.

In various embodiments, the printed circuit board comprises a first layer comprising the planar inductor and a second layer comprising the wide band gap device.

In various embodiments, the wide band gap device comprises a transistor.

A method of powering an excimer lamp is disclosed. The method comprises switching a wide band gap device from an OFF state to an ON state, charging an inductor, switching the wide band gap device from the ON state to the OFF state, and discharging the inductor to the excimer lamp.

In various embodiments, charging the inductor is performed in response to the wide band gap device switching from the OFF state to the ON state.

In various embodiments, the method further comprises receiving a direct current voltage from a power source by the wide band gap device.

In various embodiments, the method further comprises generating a pulse output voltage waveform in response to the inductor discharging to the excimer lamp.

The foregoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

DETAILED DESCRIPTION

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not of limitation. Furthermore, any reference to singular includes plural embodiments, and any reference to more than one component or step may include a singular embodiment or step. Also, any reference to attached, fixed, connected, or the like may include permanent, removable, temporary, partial, full or any other possible attachment option. Additionally, any reference to without contact (or similar phrases) may also include reduced contact or minimal contact. It should also be understood that unless specifically stated otherwise, references to "a," "an" or "the" may include one or more than one and that reference to an item in the singular may also include the item in the plural. Further, all ranges may include upper and lower values and all ranges and ratio limits disclosed herein may be combined.

As used herein, the term "wide band gap" is used to refer to a device having a semiconductor material which has a bandgap in the range of 2-4 electronvolt (eV). Examples of wide band gap semiconductor materials include Silicon Carbide (SiC) and Gallium Nitride (GaN).

As used herein, "high frequency" is used to refer to a frequency of between 50 kilohertz and 500 kilohertz (50-500 kHz).

In various embodiments, Far-UVC (at or near 222 nm wavelength light) has promise to work in occupied spaces. Excimer lamps utilize a high voltage supply and have a large gas discharge. In various embodiments, the systems and methods disclosed herein are configured to generate nanosecond pulsed power signals for an excimer lamp. Nanosecond pulsed discharge tends to be more homogenous and stable compared with sine AC voltage. Moreover, the plasma gas temperature of the excimer lamp tends to be lower compared with sine AC voltage.

In various embodiments, the sanitization systems disclosed herein, utilize an improved power supply. The improved power supply disclosed herein tend to increase the life of Far-UVC excimer lamps, lower operating temperature, and provide a more stable and homogenous gas discharge. A sanitization apparatus as disclosed herein may utilize a low voltage input (e.g., 24 VDC or 28 VDC) while generating a high frequency and high voltage (e.g., between 3 kV and 6 kV) output voltage. A power converter for the sanitization apparatus as disclosed herein may comprise a minimized footprint and/or profile while achieving a high power density.

Figure 1:
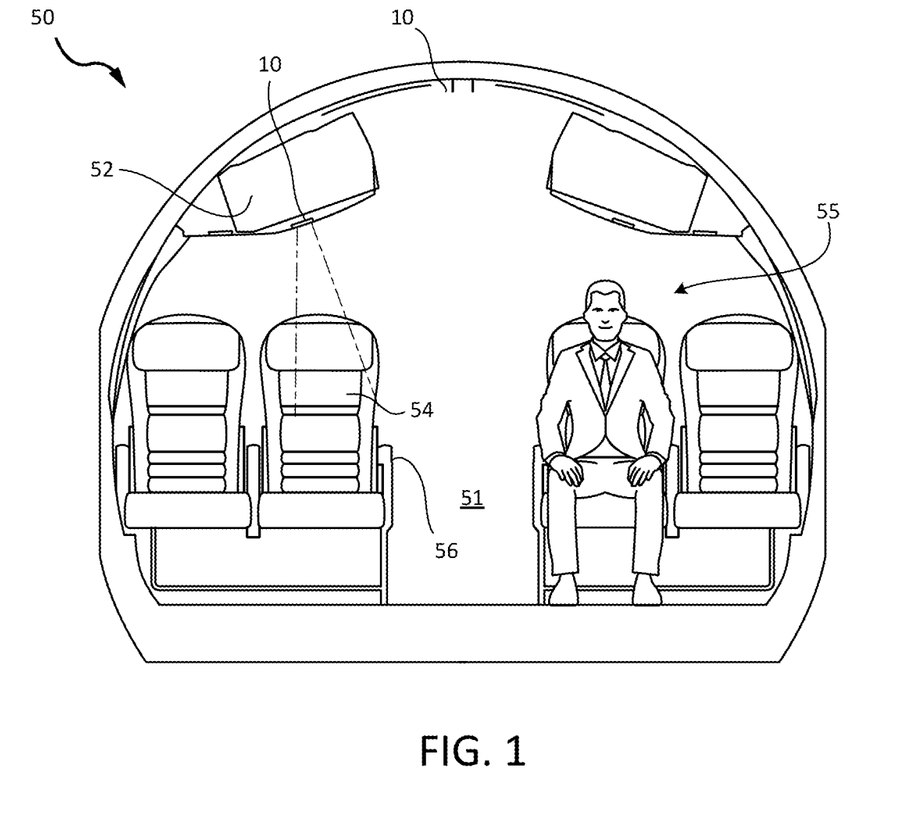
FIG. 1 illustrates a view of a cabin of an aircraft, in accordance with various embodiments.

With reference to FIG. 1, a cabin 51 of an aircraft 50 is shown, according to various embodiments. The aircraft 50 may be any aircraft such as an airplane, a helicopter, or any other aircraft. The aircraft 50 may include various lighting systems 10 that emit visible light to the cabin 51. Pathogens, such as viruses and bacteria, may remain on surfaces of the cabin 51, and these remaining pathogens may result in indirect contact transmission to other people (e.g., subsequent passengers). For example, the cabin 51 may include overhead bins 52, passenger seats 54 for supporting passengers 55, handles 56, lavatory surfaces, and other structures/surfaces upon which active pathogens may temporarily reside. As will be discussed further below, in order to reduce the transmission/transfer of pathogens between passengers, one or more of the lighting systems 10 may blend disinfecting electromagnetic radiation output into the visible light in order to facilitate disinfection of the cabin 51 (e.g., during flights and/or between flights). The lighting systems 10 may be broken down into different addressable lighting regions that could be used on an aircraft. For example, the regions on an aircraft may include sidewall lighting, cross-bin lighting, over wing exit lighting, ceiling lighting, direct lighting, flex lights, reading lights, dome lights, lavatory lights, mirror lights, cockpit lights, cargo lights, etc. The regional breakdown of the lighting system allows lighting control over broad areas of the aircraft. In various embodiments, lighting system 10 may be disposed in/incorporated by a passenger service unit (PSU) for a row of seats. As such, a lighting system 10 could be provided for each row of an aircraft, as well as for each section of different sections of a given row of an aircraft.

Figure 2:
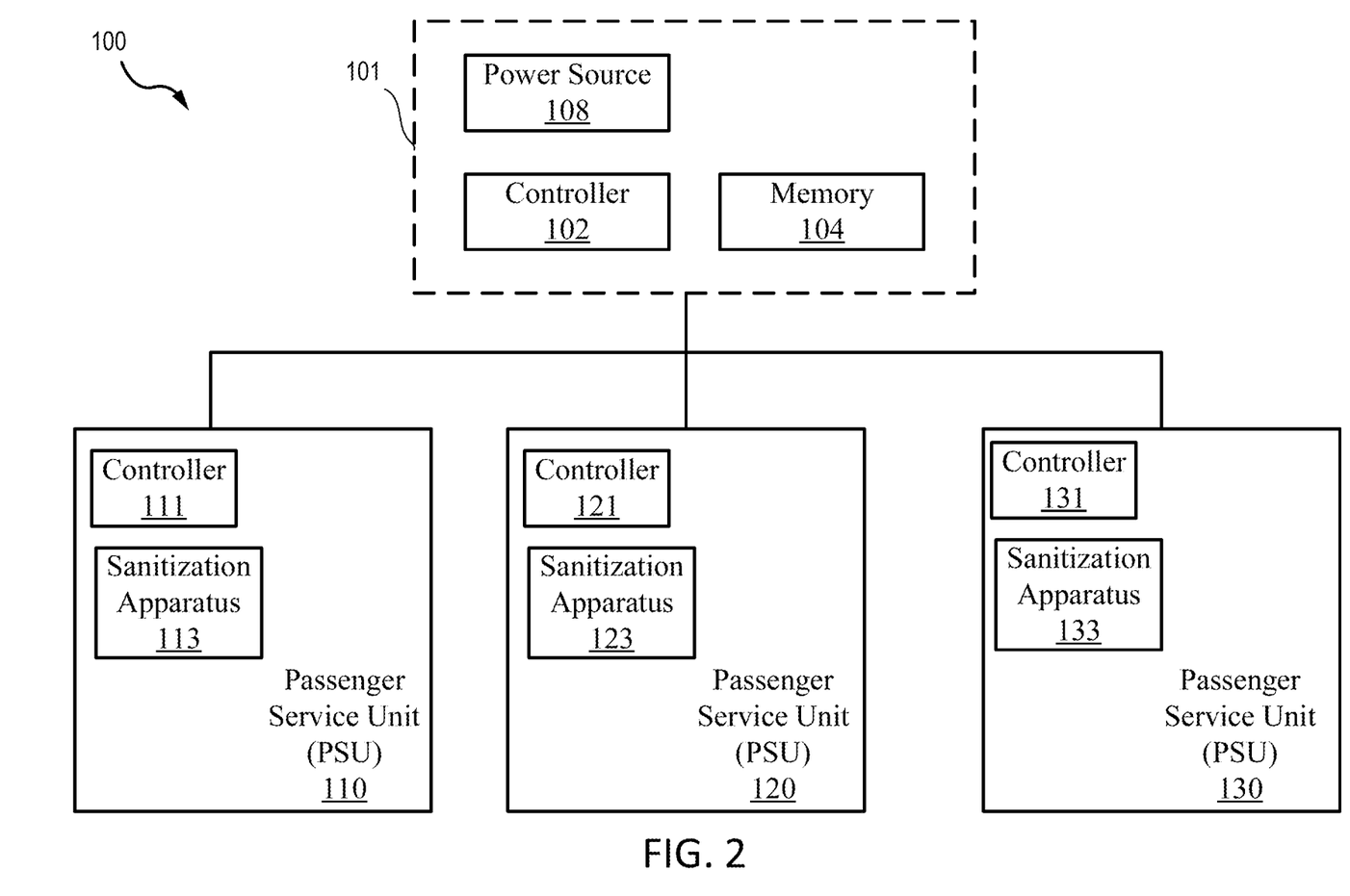
FIG. 2 illustrates a schematic view of a sanitization system, in accordance with various embodiments.

Referring now to FIG. 2 a schematic view of a sanitization system 100 for an aircraft cabin, is illustrated, in accordance with various embodiments. In various embodiments, the sanitization system 100 comprises a main control system 101 and a plurality of PSUs (e.g., first PSU 110, second PSU 120, third PSU 130, etc.). Although illustrated as including three PSUs, the number of PSUs of a sanitization system 100 is not limited in this regard. For example, a PSU may be disposed in each row of seats disposed in a respective column of an aircraft cabin. For example, a cabin with 50 rows and 3 columns may have 150 PSUs (e.g., each row in each column having a PSU). In various embodiments, the PSUs are not limited to rows in the aircraft cabin and may be placed throughout the aircraft cabin as well. For example, PSUs, in accordance with the present disclosure, may be disposed in the lavatory, aisles, cockpit, or any other area of an aircraft cabin where it may be desirable to have sanitization.

In various embodiments, the main control system 101 includes a controller 102 and a memory 104 (e.g., a database or any appropriate data structure; hereafter "memory 104" also may be referred to as "database 104"). The controller 102 may include one or more logic devices such as one or more of a central processing unit (CPU), an accelerated processing unit (APU), a digital signal processor (DSP), a field programmable gate array (FPGA), an application specific integrated circuit (ASIC), or the like (e.g., controller 102 may utilize one or more processors of any appropriate type/configuration, may utilize any appropriate processing architecture, or both). In various embodiments, the controller 102 may further include any non-transitory memory known in the art. The memory 104 may store instructions usable by the logic device to perform operations. Any appropriate computer-readable type/configuration may be utilized as the memory 104. Any appropriate data storage architecture may be utilized by the memory 104.

The database 104 may be integral to the control system 101 or may be located remote from the control system 101. The controller 102 may communicate with the database 104 via any wired or wireless protocol. In that regard, the controller 102 may access data stored in the database 104. In various embodiments, the controller 102 may be integrated into computer systems onboard an aircraft. Furthermore, any number of conventional techniques for electronics configuration, signal processing and/or control, data processing and the like may be employed. Also, the processes, functions, and instructions may include software routines in conjunction with processors, etc.

System program instructions and/or controller instructions may be loaded onto a non-transitory, tangible computer-readable medium having instructions stored thereon that, in response to execution by the processor, cause the controller 102 to perform various operations. The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

The instructions stored on the memory 104 of the controller 102 may be configured to perform various operations, such as performing cleaning schedules between flights, performing cleaning schedules at predetermined intervals, cleaning a specific row in response to a trigger (i.e., a sneeze or the like), etc.

In various embodiments, the main control system 101 from FIG. 2 further comprises a power source 108. The power source 108 may comprise any power source known in the art, such as a battery, a solar source, an alternating current (AC) source, a direct current (DC) source, a rechargeable source, or the like.

In various embodiments, the main control system 101 is in operable communication with each PSU in the plurality of PSUs (e.g., PSUs 110, 120, 130). In various embodiments, each PSU comprises a local controller (e.g., controllers 111, 121, 131). Each local controller (e.g., controllers 111, 121, 131) may be in accordance with main controller 102. For example, each local controller (e.g., controllers 111, 121, 131) may include one or more logic devices such as one or more of a central processing unit (CPU), an accelerated processing unit (APU), a digital signal processor (DSP), a field programmable gate array (FPGA), an application specific integrated circuit (ASIC), or the like (e.g., controllers 111, 121, 131 may utilize one or more processors of any appropriate type/configuration, may utilize any appropriate processing architecture, or both). In various embodiments, the controllers 111, 121, 131 may each further include any non-transitory memory that is known in the art. The memory may store instructions usable by the logic device to perform operations. Any appropriate computer-readable type/configuration may be utilized as the memory. Any appropriate data storage architecture may be utilized by the memory.

In various embodiments, each PSU (e.g., PSUs 110, 120, 130) may comprise a sanitization apparatus (e.g., sanitization apparatus 113, 123, 133). As described further herein, the controller 102 may command the various local controllers (e.g., controllers 111, 121, 131) to instruct the devices therein. In various embodiments, the power source 108 is sized and configured to power all of the sanitization apparatus (e.g., sanitization apparatus 113, 123, 133) of all of the PSUs (e.g., PSUs 110, 120, 130, etc.) of sanitization system 100.

In various embodiments, each sanitization apparatus (e.g., sanitization apparatus 113, 123, 133) may be connected via digital communications, discrete communications, or wireless communications to a respective local controller (e.g., controllers 111, 121, 131).

In various embodiments, the sanitization apparatus 113 may comprise a Far-UVC light source. Sanitization apparatus 113 may comprise an excimer lamp. In various embodiments, any light source capable of outputting a light with a wavelength of about 222 nm is within the scope of this disclosure. Sanitization apparatus 113 may be configured to generate a Far-UVC light having a wavelength of between 200 and 230 nm, in accordance with various embodiments. Sanitization apparatus 113 may be configured to generate a Far-UVC light having a wavelength of between 200 and 225 nm, in accordance with various embodiments. Sanitization apparatus 113 may be configured to generate a Far-UVC light having a wavelength of between 207 and 225 nm, in accordance with various embodiments. Sanitization apparatus 113 may be configured to generate a Far-UVC light having a wavelength of about 222 nm, wherein the term "about" in this regard can only refer to a wavelength of 222 nm±15 nm. In various embodiments, the sanitization apparatus 113 is in operable communication with local controller 111 and/or a main controller 102. In this regard, in response to receiving a signal from a controller (e.g., local controller 111 and/or a main controller 102), the light source may be activated and generate Far-UVC disinfecting light.

Figure 3:
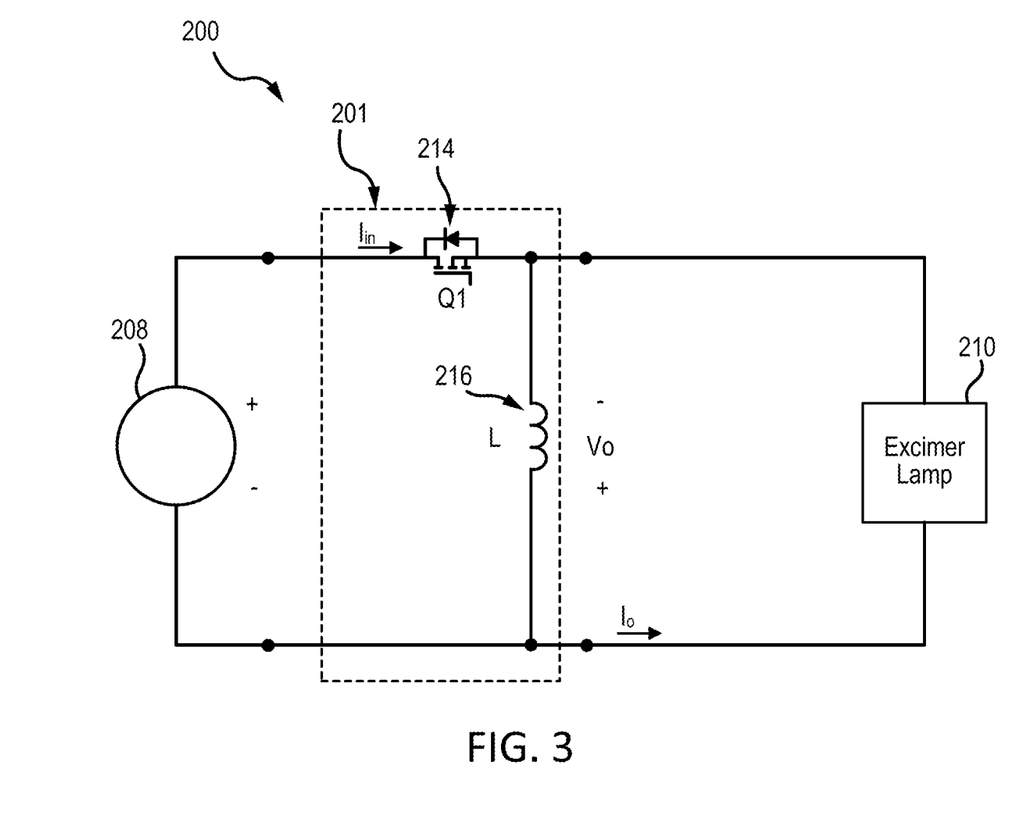
FIG. 3 illustrates a circuit diagram of a sanitization apparatus connected with a power source, in accordance with various embodiments.

With reference to FIG. 3, a schematic view of a sanitization apparatus 200 connected with a power source 208 is illustrated, in accordance with various embodiments. In various embodiments, sanitization apparatus 200 is similar to sanitization apparatus 113 of FIG. 2. Sanitization apparatus 200 includes an excimer lamp 210. Sanitization apparatus 200 includes a power converter 201 for supplying power to excimer lamp 210. Power converter 201 may receive an input power signal from power source 208. Power converter 201 may receive an input power signal from power source 208 comprising a DC power signal (e.g., 24 VDC or 28 VDC).

Power converter 201 comprises an electric circuit comprising a wide band gap (WBG) device 214 and an inductor 216. In various embodiments, the topology of power converter 401 may allow for a desired output voltage shape for excimer lamp 210 without the use of a transformer.

In various embodiments, WBG device 214 comprises a transistor selectively switchable between an ON state and an OFF state (e.g., by controller 102 and/or controller 111 of FIG. 2). In various embodiments, WBG device 214 comprises a Silicon Carbide (SiC) MOSFET. WBG device 214 may comprise a single SiC MOSFET. In various embodiments, WBG device 214 comprises a plurality of Gallium Nitride (GaN) MOSFETS arranged in series. With WBG device 214 in the ON state, the inductor 216 is configured to receive electric current ($I_{in}$) from power source 208. Stated differently, in response to WBG device 214 being switched to the ON state, inductor 216 may receive electric current ($I_{in}$) from power source 208 via WBG device 214. With WBG device 214 in the OFF state, the inductor 216 is electrically disconnected from power source 208.

Figure 4A:
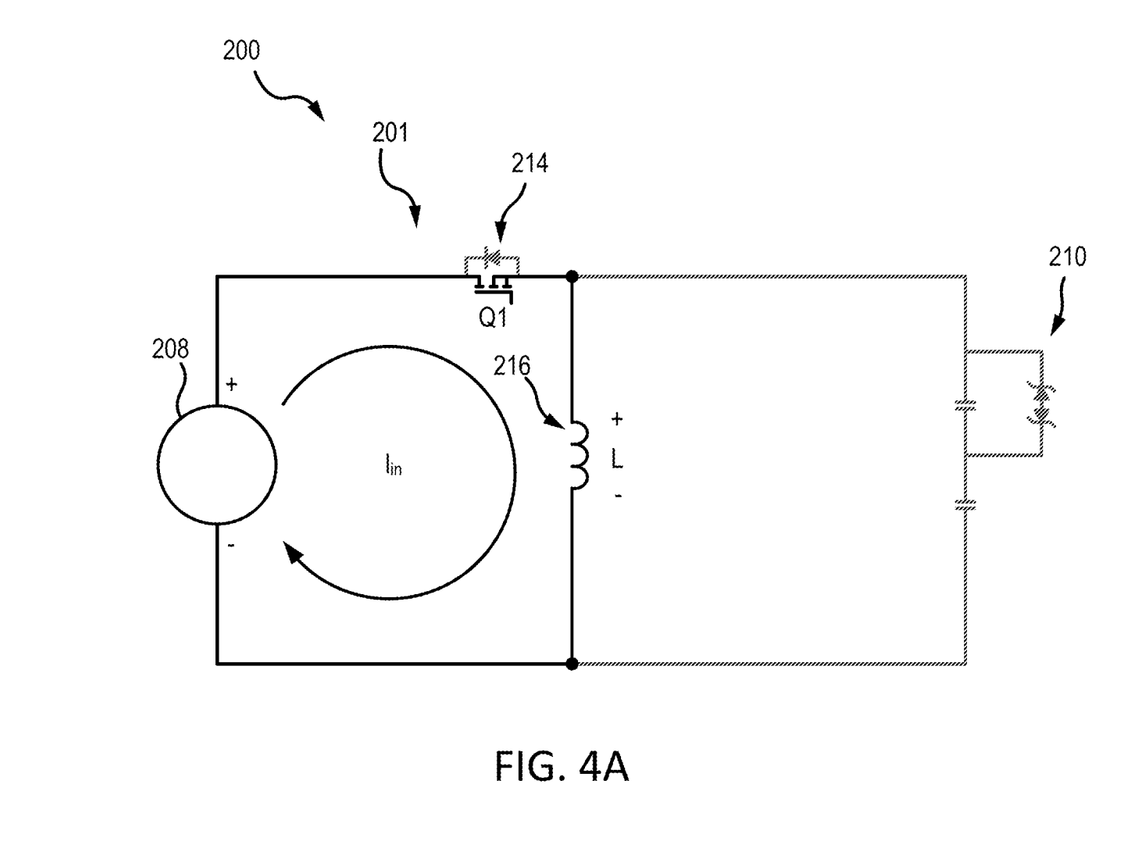
FIG. 4A and FIG. 4B illustrate the flow of current through the power converter of FIG. 3 in a first mode and a second mode, respectively, during operation of the sanitization apparatus, in accordance with various embodiments.
Figure 4B:
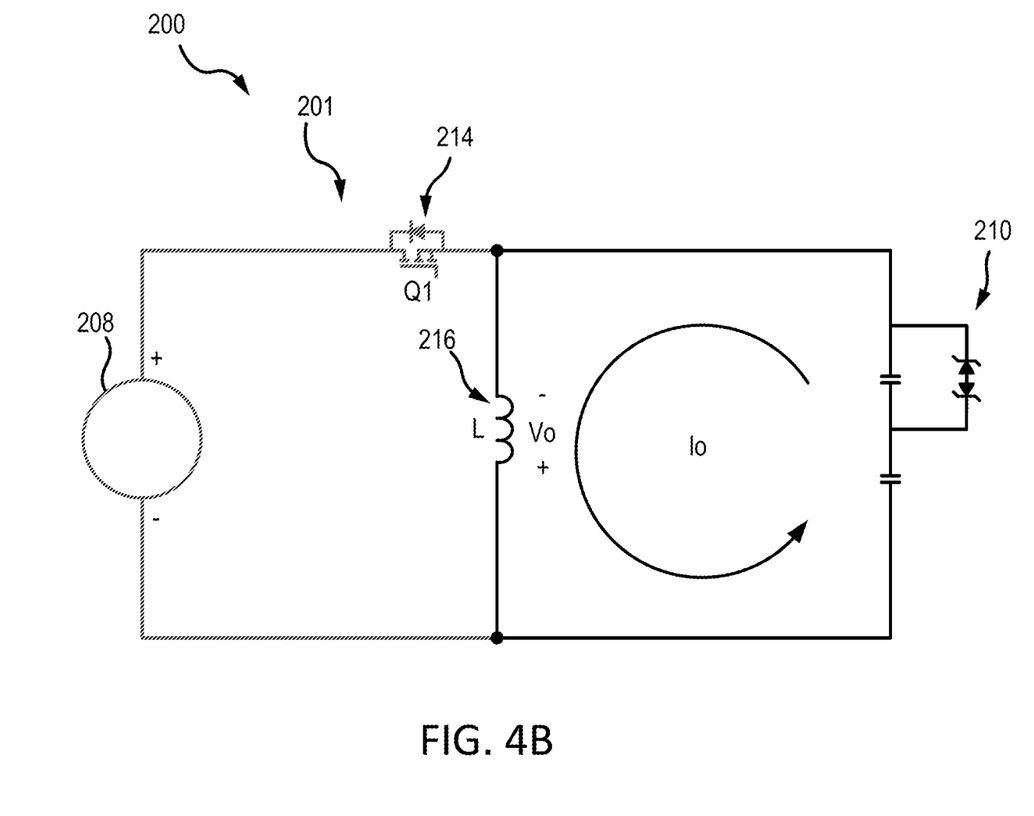

WBG device 214 may be selectively switched between its ON and OFF states to generate a nanosecond pulse output voltage ($V_o$). With reference to FIG. 4A, sanitization apparatus 200 is illustrated with WBG device 214 in an ON state (also referred to herein as a first mode). In this first mode, Q1 switch is turned ON. In this first mode, inductor 216 may be charged by the input low voltage DC power (e.g., 28V DC) of power source 208. With reference to FIG. 4B, sanitization apparatus 200 is illustrated with WBG device 214 in an OFF state (also referred to herein as a second mode). In the second mode, Q1 switch is turned OFF. In the second mode, inductor 216 may discharge electric current Io into the excimer lamp 210. After the dielectric barrier discharge, the inductor charging loop (i.e., see FIG. 4A) may be repeated. In this regard, inductor 216 may be configured to receive an electric power in response to WBG device 214 switching to the ON state and configured to discharge the electric power into excimer lamp 210 in response to WBG device 214 switching to the OFF state. As WBG device 214 switches between the ON and OFF states, output voltage ($V_o$) and output current $I_o$ may be generated by power converter 201 (e.g., see output power signals at FIG. 3, FIG. 4A, FIG. 4B, FIG. 5A, and FIG. 5B).

Figure 5A:
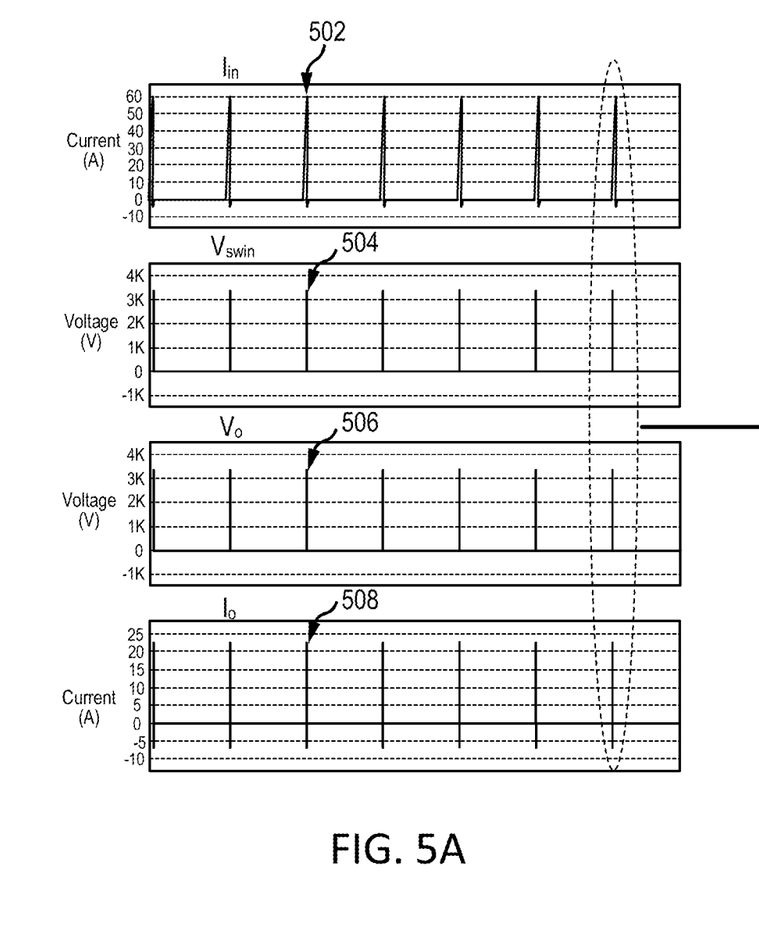
FIG. 5A and FIG. 5B illustrate plots of electric signals of the sanitization apparatus of FIG. 3 during operation of the sanitization apparatus, in accordance with various embodiments.
Figure 5B:
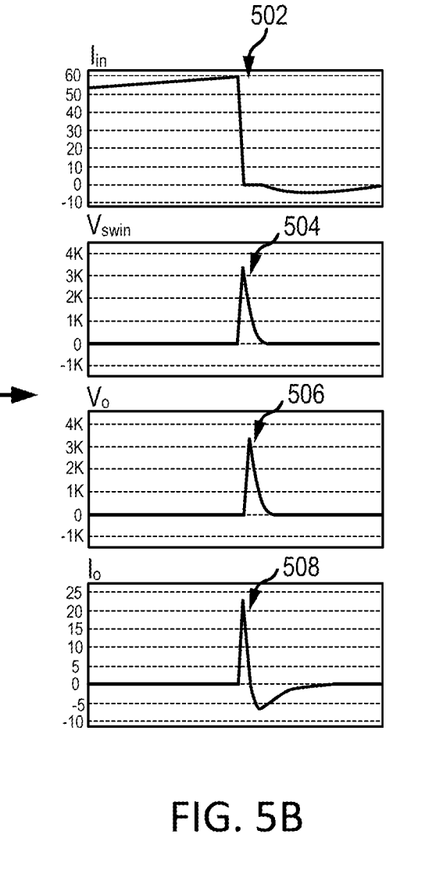

With reference to FIG. 5A and FIG. 5B, various electronic signals of sanitization apparatus 200 (see FIG. 3) during operation are illustrated, in accordance with various embodiments. With combined reference to FIG. 3 and FIG. 5A, during operation of sanitization apparatus 200, power converter 201 may supply electric power comprising an output voltage ($V_o$) waveform suitable for powering a 222 nm Far-UVC excimer lamp (e.g., excimer lamp 210). Suitable output voltages include, but are not limited to, bipolar nano second pulse waves, unipolar nano second pulse waves, and high frequency sine waves. As used herein, "high frequency" may refer to a frequency of between 50 and 500 kilohertz (50-500 kHz). FIG. 5A illustrates a unipolar nano second pulse waveform 506, in accordance with various embodiments. Waveform 506 may comprise a peak voltage of between 3 and 6 kilovolts (3-6 kV). Waveform 506 may comprise a pulse duration of less than 200 nanoseconds. In various embodiments, the pulse duration is between 0.1 nanoseconds and 200 nanoseconds. Waveform 506 may be the output voltage across inductor 216.

During operation of sanitization apparatus 200, power converter 201 may supply electric power comprising an output current Io waveform suitable for powering a 222 nm Far-UVC excimer lamp (e.g., excimer lamp 210). Suitable output currents include, but are not limited to, bipolar nano second pulse waves, unipolar nano second pulse waves, and high frequency sine waves. FIG. 5A illustrates a unipolar nano second pulse waveform 508, in accordance with various embodiments. Waveform 508 may comprise a peak current of between 15 and 45 amperes (15-45 A). Waveform 508 may comprise a pulse duration of less than 200 nanoseconds. In various embodiments, the pulse duration is between 0.1 nanoseconds and 200 nanoseconds. Waveform 508 may be the output current from inductor 216.

FIG. 5A further illustrates input current ($I_{in}$) waveform 502. Waveform 502 may be the current through excimer lamp 210 during operation. FIG. 5A further illustrates switch input voltage ($V_{swin}$) waveform 504. Waveform 504 may be the voltage across excimer lamp 210 during operation. The voltage across excimer lamp 210 may be substantially similar to output voltage ($V_o$). FIG. 5B illustrates enlarged views of a single pulse of the waveforms of FIG. 5A (i.e., waveforms 502, 504, 506, 508).

Figure 6:
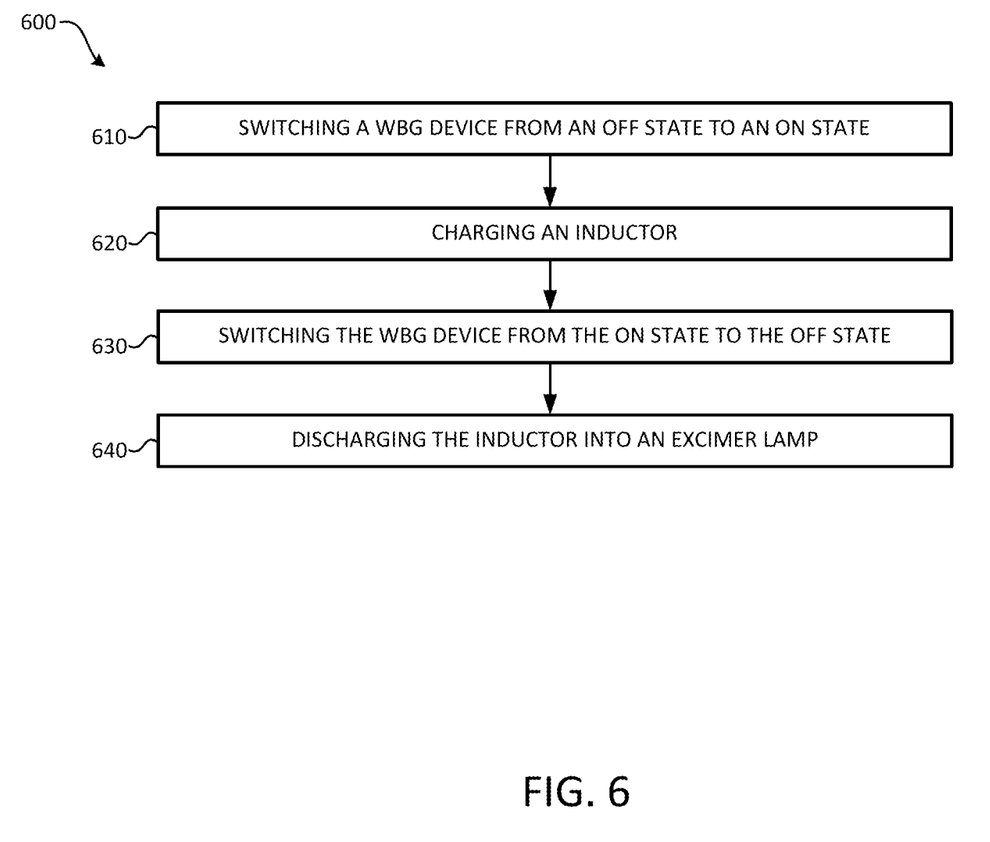
FIG. 6 illustrates a flow chart of a process for powering a sanitization apparatus, in accordance with various embodiments.

With reference to FIG. 6, a method 600 is illustrated, in accordance with various embodiments. Method 600 may be for powering a 222 nm Far-UVC excimer lamp. Method 600 includes switching a WBG device from an OFF state to an ON state (step 610). Method 600 includes charging an inductor in response to the WBG device switching from the OFF state to the ON state (step 620). Method 600 includes switching the WBG device from the ON state to the OFF state (step 630). Method 600 includes discharging the inductor into an excimer lamp in response to the WBG device switching from the ON state to the OFF state.

With combined reference to FIG. 3 and FIG. 6, step 610 may include switching (e.g., by controller 102 and/or controller 111 of FIG. 2) WBG device 214 from an OFF state to an ON state. Step 620 may include charging inductor 216 in response to WBG device 214 switching from the OFF state to the ON state. Step 640 may include switching WBG device 214 from the ON state to the OFF state. Step 650 may include discharging inductor 216 into excimer lamp 210 in response to WBG device 214 switching from the ON state to the OFF state.

Figure 7:
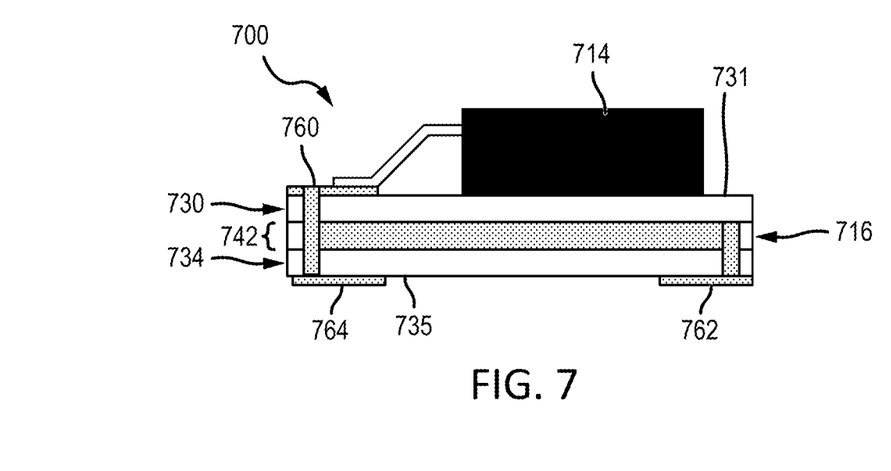
FIG. 7 illustrates a power converter circuit board for a sanitization apparatus, the power converter circuit board having an embedded planar capacitor and an embedded planar inductor, in accordance with various embodiments.

With reference to FIG. 7, a printed circuit board (PCB) 700 is illustrated, in accordance with various embodiments. In various embodiments, power converter 201 of FIG. 3 may comprise PCB 700. PCB 700 may comprise a planar inductor 716. In various embodiments, inductor 216 of FIG. 3 is similar to planar inductor 716. PCB 700 may comprise a layer 742 (also referred to herein as a first layer) comprising planar inductor 716. Planar inductor 716 may be embedded in PCB 700. PCB 700 may include a top layer 730. Top layer 730 may comprise an external surface 731. PCB 700 may include a bottom layer 734 defining a second external surface 735. Planar inductor 716 may be located internally from bottom layer 734. Planar inductor 716 may be located between bottom layer 734 and top layer 730.

PCB 700 may further comprise a WBG device 714. WBG device 714 may be disposed at external surface 731. An electrical contact 760 may be disposed at external surface 731. Electrical contact 760 may comprise a conductive material, such as copper for example. An electrical contact 762 may be disposed at second external surface 735. Electrical contact 762 may comprise a conductive material, such as copper for example. WBG device 714 may be electrically coupled to electrical contact 760. Electrical contact 760 may be electrically coupled with electrical contact 762 via planar inductor 716.

An electrical contact 764 may be disposed at second external surface 735. Electrical contact 764 may comprise a conductive material, such as copper for example. Electrical contact 760 may be electrically coupled with electrical contact 764 via planar inductor 716. Electrical contact 762 may be coupled at opposite ends of the windings of inductor 716, in accordance with various embodiments.

Top layer 730 and bottom layer 734 may each comprise a non-conductive substrate. In this regard, top layer 730 and bottom layer 734 may be electrically insulating layers.

Figure 8:
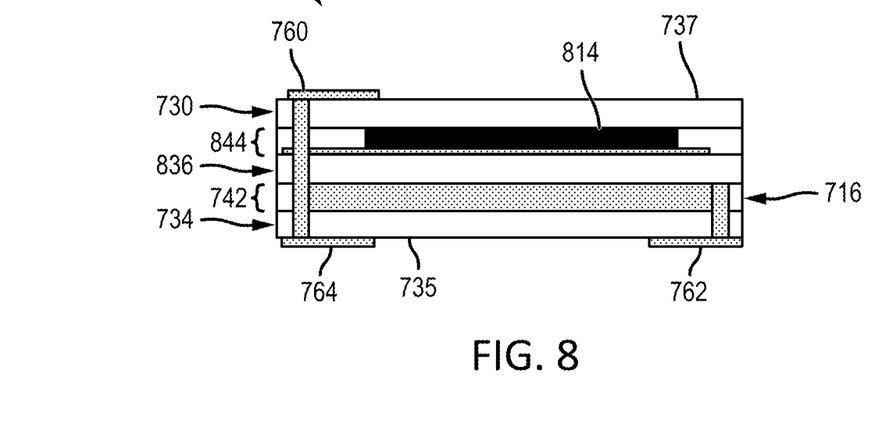
FIG. 8 illustrates a power converter circuit board for a sanitization apparatus, the power converter circuit board having an embedded wide band gap device, an embedded planar capacitor, and an embedded planar inductor, in accordance with various embodiments.

With reference to FIG. 8, a PCB 800 is illustrated, in accordance with various embodiments. PCB 800 may be similar to PCB 700 of FIG. 7, except that PCB 800 comprises an embedded WBG device 814. With respect to FIG. 8, elements with like element numbering, as depicted in FIG. 7, are intended to be the same and will not necessarily be repeated for the sake of clarity. In various embodiments, power converter 201 of FIG. 3 may comprise PCB 800. PCB 800 may comprise embedded WBG device 814. In various embodiments, WBG device 214 of FIG. 3 is similar to WBG device 814. PCB 800 may comprise a layer 844 (also referred to herein as a second layer) comprising WBG device 814. WBG device 814 may be located internally from top layer 730.

PCB 800 may include an internal layer 836 located between WBG device 814 and planar inductor 716. Internal layer 836 may comprise a non-conductive substrate. In this regard, internal layer 836 may be an electrically insulating layer.

Figure 9:
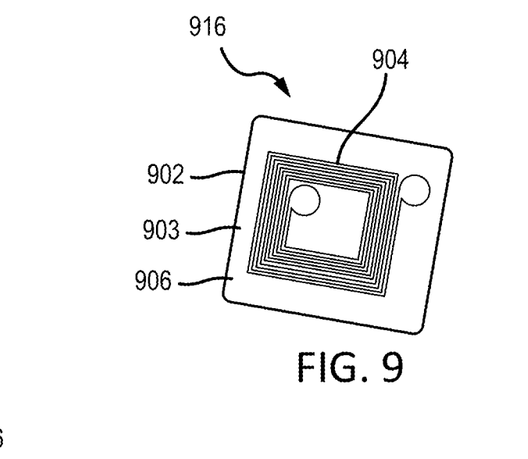
FIG. 9 illustrates a perspective view of a planar inductor, in accordance with various embodiments.

With reference to FIG. 9, a planar inductor 916 is illustrated, in accordance with various embodiments. Planar inductor 916 may comprise a planar body 902 comprising an electrically insulating material 903 and a plurality of windings 904 arranged on a planar surface 906 of the planar body 902.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is intended to invoke 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, it should be understood that any of the above described concepts can be used alone or in combination with any or all of the other above described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible in light of the above teaching.

What is claimed is:

1. A sanitization apparatus comprising:
   an excimer lamp configured to emit Far-UVC light; and
   a power converter comprising a printed circuit board, a wide band gap device embedded in the printed circuit board and comprising a transistor, and a planar inductor embedded in the printed circuit board,
   wherein the printed circuit board comprises a first layer comprising the planar inductor and a second layer comprising the wide band gap device, and
   wherein the wide band gap device is selectively switchable between a first mode wherein the planar inductor is configured to be electrically charged and a second mode wherein the planar inductor is configured to be electrically discharged to the excimer lamp.

2. The sanitization apparatus of claim 1, wherein the wide band gap device is in an ON state in the first mode and the wide band gap device is in an OFF state in the second mode.

3. The sanitization apparatus of claim 2, further comprising a DC power supply configured to charge the planar inductor when the wide band gap device is in the second mode.

4. The sanitization apparatus of claim 1, wherein the planar inductor is connected across the excimer lamp.

5. A power converter for an excimer lamp comprising:
   a printed circuit board;
   a wide band gap device embedded in the printed circuit board and comprising a transistor selectively switchable between an ON state in a first mode and an OFF state in a second mode; and
   a planar inductor embedded in the printed circuit board and configured to receive an electric power in response to the wide band gap device switching to the first mode and configured to discharge the electric power into the excimer lamp in response to the wide band gap device switching to the second mode;
   wherein the printed circuit board comprises a first layer comprising the planar inductor and a second layer comprising the wide band gap device.

6. A method of powering an excimer lamp configured to emit Far-UVC light, the method comprising:
   switching a wide band gap device from an OFF state to an ON state, wherein the wide band gap device is in the ON state in a first mode;
   charging a planar inductor;
   switching the wide band gap device from the ON state to the OFF state, wherein the wide band gap device is in the OFF state in a second mode; and
   discharging the planar inductor to the excimer lamp,
   wherein the planar inductor is embedded in a first layer of a printed circuit board of a power converter,
   the wide band gap device is embedded in a second layer of the printed circuit board, and
   the wide band gap device comprises a transistor.

7. The method of claim 6, wherein charging the planar inductor is performed in response to the wide band gap device switching from the OFF state to the ON state.

8. The method of claim 7, further comprising receiving a direct current voltage from a power source by the wide band gap device.

9. The method of claim 8, further comprising generating a pulse output voltage waveform in response to the planar inductor discharging to the excimer lamp.

10. The sanitization apparatus of claim 4, wherein:
   in the first mode, a polarity of the planar inductor is in a first direction; and
   in the second mode, the polarity of the planar inductor is in a second direction, opposite the first direction.

11. The power converter of claim 5, wherein:
   the planar inductor is connected across the excimer lamp;
   in the first mode, a polarity of the planar inductor is in a first direction; and
   in the second mode, the polarity of the planar inductor is in a second direction, opposite the first direction.

12. The method of claim 6, wherein:
   the planar inductor is connected across the excimer lamp;
   in the first mode, a polarity of the planar inductor is in a first direction; and
   in the second mode, the polarity of the planar inductor is in a second direction, opposite the first direction.

\* \* \* \* \*